US012329662B2

(12) United States Patent
Westgard et al.

(10) Patent No.: US 12,329,662 B2
(45) Date of Patent: Jun. 17, 2025

(54) BIOMECHANICAL MOTION DEVICE FOR HUMAN GAIT LOAD REPLICATION

(71) Applicant: Ekso Bionics Holdings, Inc., San Rafael, CA (US)

(72) Inventors: Samuel K. Westgard, Guilford, CT (US); Ryan J. Farris, Mechanicsburg, PA (US)

(73) Assignee: Ekso Bionics Holdings, Inc., San Rafael, CA (US)

( * ) Notice: Subject to any disclaimer, the term of this patent is extended or adjusted under 35 U.S.C. 154(b) by 666 days.

(21) Appl. No.: 17/774,319

(22) PCT Filed: Oct. 20, 2020

(86) PCT No.: PCT/US2020/056411
§ 371 (c)(1),
(2) Date: May 4, 2022

(87) PCT Pub. No.: WO2022/086498
PCT Pub. Date: Apr. 28, 2022

(65) Prior Publication Data
US 2022/0387196 A1    Dec. 8, 2022

(51) Int. Cl.
*A61F 2/76*    (2006.01)
*A61B 5/00*    (2006.01)
(Continued)

(52) U.S. Cl.
CPC .............. *A61F 2/76* (2013.01); *A61B 5/1038* (2013.01); *A61B 5/112* (2013.01); *A61B 5/4851* (2013.01);
(Continued)

(58) Field of Classification Search
CPC ...... A61F 2/76; A61F 2/60; A61F 2002/7695; A61B 5/1038; A61B 5/112; A61B 5/4851; A61B 5/6828; A61B 5/6829
See application file for complete search history.

(56) References Cited

U.S. PATENT DOCUMENTS 4,130,007 A    12/1978    Hayashi
4,432,223 A    2/1984    Paquette et al.

FOREIGN PATENT DOCUMENTS

CN    101357085 A    2/2009
CN    101856286 A    10/2010
(Continued)

OTHER PUBLICATIONS

CN-109431513-A, English Translation (Year: 2019).*
CN-111568612-A, English Translation (Year: 2020).*
WO-2020245536-A1, English Translation (Year: 2020).*

*Primary Examiner* — Ryan D Walsh
(74) *Attorney, Agent, or Firm* — Renner, Otto, Boisselle & Sklar, LLP

(57) ABSTRACT

A biomechanical motion device employs a plurality of actuator cylinders to generate forces representative of human gait loading. The biomechanical motion device includes a crosshead that is manipulated vertically by a set of two vertical pneumatic cylinders, and the crosshead is mounted to two vertical shafts on linear bearings that guide the crosshead in the vertical direction. The biomechanical motion device further includes a horizontal slide system that incorporates a linear carriage rail mounted flush to the bottom of the crosshead. The linear carriage rail guides a sliding carriage, and a custom bracket is mounted to the sliding carriage. Attached to the bracket is a pivot shaft, and the shaft serves as a simulated knee joint about which a lower leg assembly can be rotated. Horizontal motion collinear with the carriage rail of the simulated knee joint (Continued)

connection is generated using a set of two horizontal pneumatic cylinders. This horizontal motion causes the lower leg assembly to pivot about where a prosthetic foot contacts a bottom contact plate during gait to rotate about the pinned knee joint.

20 Claims, 8 Drawing Sheets

(51) Int. Cl.
    *A61B 5/103*     (2006.01)
    *A61B 5/11*     (2006.01)
    *A61F 2/60*     (2006.01)

(52) U.S. Cl.
    CPC ........... *A61B 5/6828* (2013.01); *A61B 5/6829* (2013.01); *A61F 2/60* (2013.01); *A61F 2002/7695* (2013.01)

(56) References Cited

FOREIGN PATENT DOCUMENTS

| | | | | |
|---|---|---|---|---|
| CN | 203154010 U | | 8/2013 | |
| CN | 104504984 A | | 4/2015 | |
| CN | 107468387 A | | 12/2017 | |
| CN | 109431513 A | * | 3/2019 | |
| CN | 110063822 A | | 7/2019 | |
| CN | 111568612 A | * | 8/2020 | ........... A61F 2/4684 |
| KR | 20200087499 A | | 7/2020 | |
| WO | WO-2020245536 A1 | * | 12/2020 | ........... A43D 999/00 |

* cited by examiner

BIOMECHANICAL MOTION DEVICE FOR HUMAN GAIT LOAD REPLICATION

This application is a national phase of International Application No. PCT/US2020/056411 filed Oct. 20, 2020, which is hereby incorporated herein by reference in its entirety.

FIELD OF INVENTION

The present application relates to mobility assistance devices, such as orthotic and prosthetic devices, and more particularly to a biomechanical motion device that replicates human gait motion for the purpose of testing mobility assistance devices, such as for example for testing a lower leg or prosthetic foot device.

BACKGROUND OF THE INVENTION

Many health conditions result in significant impairment to mobility, which may be associated with varying degrees of mobility impairment. The large population of persons afflicted with such conditions include, for example, those affected by stroke, multiple sclerosis, ALS, Parkinson's disease, spinal cord injury, cerebral palsy, amputees, and many other conditions resulting from birth defects, disease, injury, or aging. To aid mobility, mobility assistance devices, such as leg orthotic devices and prosthetic devices, have been employed.

There is a need to implement effective performance and durability testing of such devices, including lower limb prosthetics, footwear, insoles, gait sensors, and the like. To attempt to perform such testing in a timely manner, biomechanical motion devices are under development to replicate the human gait. A mobility assistance device being tested, therefore, is placed in or connected to the biomechanical motion device, and the biomechanical motion device attempts to simulate or replicate a human stepping motion. By using such a biomechanical testing device, limitations of human testing, such as time, endurance, impairment levels, and the like are avoided. In addition, a biomechanical testing device should be able to accommodate testing of various types of mobility assistance devices with different sizes and configurations.

Human gait generally includes two main phases: a stance phase and a swing phase. The stance phase occurs during the time the foot is in contact with the ground, and the swing phase occurs during the time the foot is off the ground such as during stepping. These phases can further be broken down into intermediate states that together form a complete gait cycle. During gait, forces are generated on the human foot that further can be broken down into horizontal and vertical ground reaction forces. Any effective biomechanical testing device should be able to replicate the various gait phases and forces that occur during human walking.

Characterization of the performance and durability of lower extremity mobility assistance devices in particular is important in developing reliable mobility assistance systems. Long term clinical testing is expensive, and gait biomechanics vary from individual to individual. In addition, conventional biomechanical testing devices that replicate gait are large and costly. It would be desirable to be able to test devices under different environmental conditions, such as at different temperatures and humidity levels. Due to their large size, however, conventional biomechanical testing devices are unlikely to fit in an environment-controlling chamber that is able to simulate such different environmental conditions. Conventional biomechanical testing devices, therefore, remain deficient.

SUMMARY OF THE INVENTION

The present application describes a biomechanical motion device for human gait load replication by replicating human gait and the forces on the tibia, ankle, and the foot during gait. The device is suitable for performance and durability testing of lower limb prosthetics, footwear, insoles, gait sensors, and the like. The biomechanical motion device replicates gait motion in such a way that the gait speed and the forces generated during gait can be varied independently. The angle of the foot relative to a contact surface at both toe off and heel strike can also be varied independently. In this manner, the biomechanical motion device replicates gait that would correspond over a wide range of human gait parameters. The biomechanical motion device replicates gait phases and forces over time and in a relatively small package as compared to conventional configurations, and in particular is sufficiently small for insertion into a typical environment-controlling chamber that is able to simulate different environmental conditions such as different temperatures and humidity levels.

In exemplary embodiments, the biomechanical motion device employs a plurality of actuator cylinders to generate forces representative of human gait loading. The actuator cylinders may be implemented as pneumatic cylinders, although other types of actuator cylinders may be employed. The actuator cylinders are controlled with a programmable logic controller (PLC) and four-way air directional control valves. The biomechanical motion device further includes a crosshead that is manipulated vertically by a set of two vertical pneumatic cylinders, and the crosshead is mounted to two vertical shafts on linear bearings that guide the crosshead in the vertical direction. The biomechanical motion device further includes a horizontal slide system that incorporates a linear carriage rail mounted flush to the bottom of the crosshead. The linear carriage rail guides a sliding carriage, and a custom bracket is mounted to this sliding carriage. Attached to this bracket is a cylindrical shaft, and the shaft serves as a simulated knee joint about which a lower leg assembly can be rotated. Horizontal motion colinear with the carriage rail of the pinned knee connection is generated using a set of two horizontal pneumatic cylinders. This horizontal motion causes the lower leg assembly to pivot about where a prosthetic foot contacts a bottom contact plate or base during gait to rotate about the pinned knee joint.

A lower leg assembly for use in the biomechanical motion device includes a round shaft to serve as a simulated tibia. A needle bearing hinge is mounted to the upper end of the shaft that rotates about the simulated knee joint. A standard prosthetic pyramid-style connector is mounted to the other end of the shaft, to which a prosthetic foot is attached for testing by the biomechanical motion device.

During operation to test a prosthetic device, the vertical cylinders raise and lower the crosshead, applying vertical forces to the lower leg assembly during the stance phase. The vertical cylinders also lift the lower leg assembly off from the bottom contact plate or base during the swing phase. The horizontal cylinders push and pull the lower leg through the stages of gait to simulate the gait motion. A heel stop block may be included in the biomechanical motion device, which serves as a hard stop for the lower leg assembly during motion. This stop block is mounted via a pinned connection and screws to the bottom contact plate. A linear pattern of holes and threads may be incorporated into the bottom contact plate to allow for the position of the heel stop block to be adjustable, and the stop block determines the position at which the heel contacts the bottom contact plate during heel strike.

In exemplary embodiments, the vertical and horizontal sets of pneumatic cylinders are controlled using one or more four-way air directional control valves. The timing and actuation of these valves is controlled using a PLC. The cadence is controlled through PLC programming, which controls the timing and duration of solenoid actuation of the control valves. Flow control is adjusted manually with a flow control screw present on the 4-way air directional control valves to adjust pneumatic flow, and in turn varying air pressure of each set of cylinders. Forces applied to the lower leg assembly thus are varied by changing pressure in each set of the vertical versus horizontal cylinders. The pressure in each set of cylinders is independently controlled with one pressure regulator for each set respectively of the vertical versus horizontal cylinders.

An aspect of the invention, therefore, is a biomechanical motion device that has a compact configuration with effective simulation of a human motion, such as for example a human gait motion. In exemplary embodiments, the biomechanical motion device includes a contact base; at least one upright shaft that extends from the contact base; a crosshead spaced apart from the contact base and that is moveable relative to the contact base along the at least one upright shaft between a first crosshead position and a second crosshead position; a carriage rail attached to the crosshead so as to be moveable with the crosshead as the crosshead moves along the at least one upright shaft; a carriage that is slidably moveable along the carriage rail between a first carriage position and a second carriage position; a prosthetic connection assembly that is attached to the carriage so as to be moveable with the carriage as the carriage slides along the carriage rail, the prosthetic connection assembly being configured to receive a prosthetic device; and an actuator assembly configured to move the crosshead along the at least one upright shaft and the carriage along the carriage rail to move the prosthetic connection assembly through a plurality of stages that simulate a human motion.

The actuator assembly may include at least one vertical cylinder that drives movement of the crosshead along the at least one upright shaft, and at least one horizontal cylinder that drives movement of the carriage along the carriage rail. Each of the at least one vertical cylinder and the at least one horizontal cylinder may be a pneumatic cylinder. The prosthetic connection assembly may be a lower leg assembly configured to receive a prosthetic foot, and the actuator assembly is configured to move the crosshead along the at least one upright shaft and the carriage along the carriage rail to move the lower leg assembly through a plurality of stages that simulate a human gait motion. The biomechanical motion device may be incorporated as part of a biomechanical motion testing system that includes the biomechanical motion device according to any of the embodiments, and an electronic control system configured to control the actuator assembly to move the prosthetic connection assembly through the plurality of stages that simulate the human motion, such as the human gait motion. As multiple cycles of human gait motion are simulated, sensor data is gathered from the prosthetic connection assembly and/or the attached prosthetic device (e.g., leg assembly to which a prosthetic foot is attached), and the sensor data may be used by the control system to assess performance of the prosthetic device based upon the sensor data.

These and further features of the present invention will be apparent with reference to the following description and attached drawings. In the description and drawings, particular embodiments of the invention have been disclosed in detail as being indicative of some of the ways in which the principles of the invention may be employed, but it is understood that the invention is not limited correspondingly in scope. Rather, the invention includes all changes, modifications and equivalents coming within the spirit and terms of the claims appended hereto. Features that are described and/or illustrated with respect to one embodiment may be used in the same way or in a similar way in one or more other embodiments and/or in combination with or instead of the features of the other embodiments.

DETAILED DESCRIPTION

Figure 1:
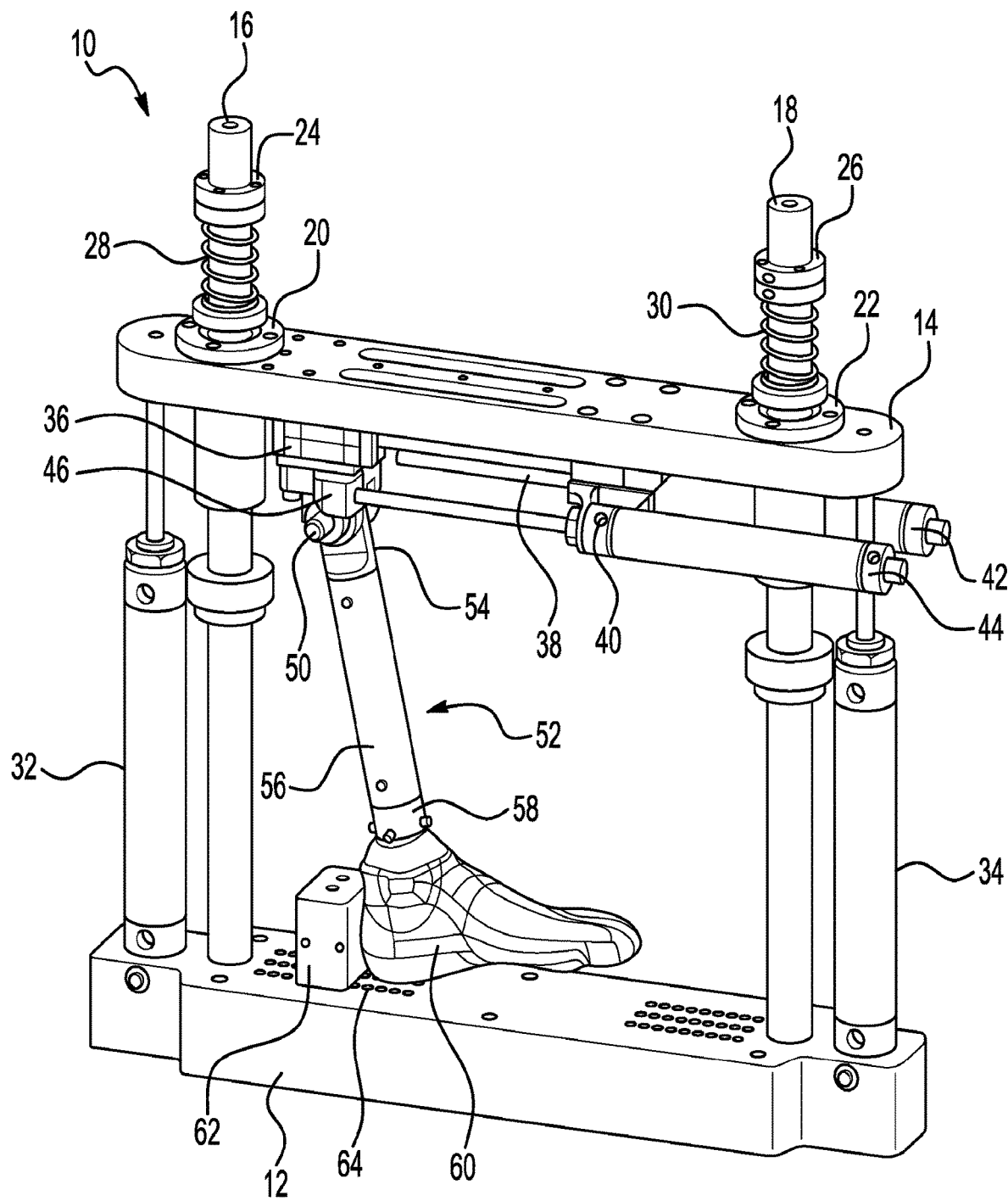
FIG. 1 and FIG. 2 are drawings depicting isometric views of an exemplary biomechanical motion device from different viewpoints, in accordance with embodiments of the present application.

Embodiments of the present application will now be described with reference to the drawings, wherein like reference numerals are used to refer to like elements throughout. It will be understood that the figures are not necessarily to scale.

The present application describes a biomechanical motion device for human gait load replication by replicating human gait and the forces on the tibia, ankle, and the foot during gait. The device is suitable for performance and durability testing of lower limb prosthetics, footwear, insoles, gait sensors, and the like. The biomechanical motion device replicates gait motion in such a way that the gait speed and the forces generated during gait can be varied independently. The angle of the foot relative to a contact surface at both toe off and heel strike can also be varied independently. In this manner, the biomechanical motion device replicates gait that would correspond over a wide range of human gait parameters. The biomechanical motion device replicates gait phases and forces over time and in a relatively small package as compared to conventional configurations, and in particular is sufficiently small for insertion into a typical environment-controlling chamber that is able to simulate different environmental conditions such as different temperatures and humidity levels.

Figure 2:
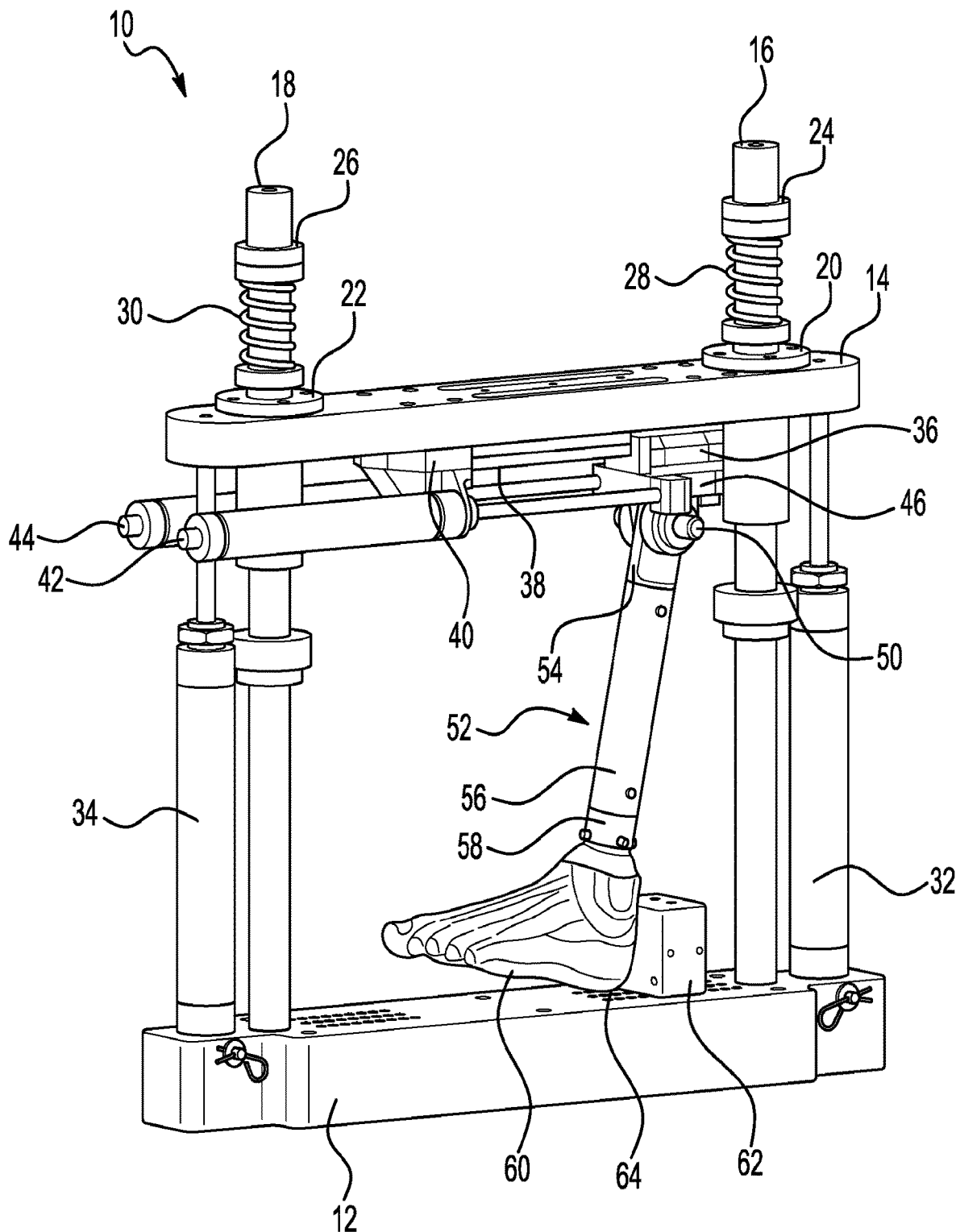

FIG. 1 and FIG. 2 are drawings depicting isometric views of an exemplary biomechanical motion device 10 from different viewpoints, in accordance with embodiments of the present application. The biomechanical motion device 10 includes a contact base 12 that is mechanically coupled to a crosshead 14 via a first upright shaft 16 and a second upright shaft 18 that extend from the contact base 12. As further detailed below, the crosshead 14 is movable in a vertical direction up or down relative to the contact base 12 along the upright shafts 16 and 18 between a first crosshead position and a second crosshead position. Any suitable number of upright shafts may be employed, although the use of two upright shafts adequately balances a compact design with controlled movement. To aid in guiding the vertical movement of the crosshead 14 relative to the contact base 12, each of the upright shafts 16 and 18 is provided with a respective vertical linear bearing 20 and 22. The upright shafts 16 and 18 further may respectively include collars 24 and 26, and return springs 28 and 30. The return springs are attached to the upright shafts and are compressible and extendable between the collars and the linear bearings, and thus the return springs operate to bias the crosshead 14 toward the first crosshead position relative to the contact base 12. In this example, the initial or first crosshead position is the position as shown in FIG. 1.

Generally, the biomechanical motion device 10 employs an actuator assembly that is configured to move the crosshead along the upright shafts between the first crosshead position and the second crosshead position. In exemplary embodiments, the actuator assembly is configured as a plurality of actuator cylinders to generate forces representative of a human motion, such as for example a human gait motion to simulate human gait loading. In the current description, the actuator cylinders are described as being implemented as pneumatic cylinders, although other types of actuator devices may be employed. Other examples of suitable actuator devices include one or a combination of hydraulic cylinders, electronic linear actuators, other linear actuators, and/or cam mechanisms. The actuator cylinders may be controlled with a programmable logic controller (PLC) and four-way air directional control valves.

To implement the vertical movement of the crosshead 14 relative to the contact base 12, the biomechanical motion device has at least one vertical cylinder that extends between the contact base 12 and the crosshead 14. In the depicted example, the actuator assembly of the biomechanical motion device includes a first vertical cylinder 32 and a second vertical cylinder 34 located adjacent opposite ends of the contact base 12 and crosshead 14 and positioned adjacent to the respective upright shafts 16 and 18. As the vertical cylinders extend and retract, the crosshead 14 moves vertically up or down relative to the contact base 12 between the first crosshead position and the second crosshead position. Any suitable number of vertical cylinders may be employed, although similarly as with using two upright shafts, the use of two vertical cylinders adequately balances a compact design with controlled movement. As referenced above, the linear bearings 20 and 22 aid in guiding the vertical movement of the crosshead 14 relative to the contact base 12. The vertical cylinders operate to implement vertical components of gait movement, as further detailed below.

The actuator assembly of the biomechanical motion device 10 further includes a horizontal slide system to implement horizontal components of the human motion, such as for example the human gait motion. In exemplary embodiments, the horizontal slide system includes a horizontal carriage 36 that rides horizontally along a linear carriage rail 38 (the carriage rail 38 is best seen in FIG. 2) relative to the contact base 12 and the crosshead 14. Accordingly, the actuator assembly further is configured to move the carriage along the carriage rail between a first carriage position and a second carriage position. The carriage rail 38 is mounted flush to or against an underside surface of the crosshead 14 by any suitable fastening mechanism. The actuator assembly of the biomechanical motion device 10 further includes a horizontal mount 40 to which there is mounted at least one horizontal cylinder that extends between the horizontal carriage 36 and the horizontal cylinder mount 40. In the depicted example, the biomechanical motion device 10 includes a first horizontal cylinder 42 and a second horizontal cylinder 44 located adjacent to and mounted on opposite sides of the horizontal carriage 36 and horizontal cylinder mount 40. As the horizontal cylinders extend and retract, horizontal carriage 36 moves horizontally left or right along the carriage rail 38 relative to the contact base 12 and crosshead 14 between the first carriage position and the second carriage position. In this manner, a sliding direction of the carriage along the carriage rail is perpendicular to a movement direction of the crosshead along the upright shafts. Any suitable number of horizontal cylinders may be employed, although similarly as with using two vertical cylinders, the use of two horizontal cylinders adequately balances a compact design with controlled movement. The horizontal cylinders operate to implement horizontal components of gait movement, as further detailed below.

The horizontal carriage rail 38 acts as a linear bearing as the carriage 36 slides along the carriage rail 38. The horizontal carriage 36 includes a carriage mount block 46 into which the rods of the horizontal cylinders are mounted. The mount block has a bracket configuration that extends oppositely from the carriage rail 38. The mount block or bracket 46 receives a pivot shaft 50 that operates as a simulated knee joint about which a lower leg assembly can be rotated as further detailed below. In general, the horizontal extension or retraction of the horizontal cylinders 42 and 44 imparts movement to the lower leg assembly to pivot about where a lower limb prosthetic, such as a prosthetic foot, contacts the contact base 12 during gait to rotate about the pinned simulated knee joint.

The biomechanical motion device 10 includes a prosthetic connection assembly 52 that is attached to the carriage so as to be moveable with the carriage as the carriage slides along the carriage rail, the prosthetic connection assembly being configured to receive a prosthetic device to be tested using the biomechanical device. Insofar as the carriage is mounted to the crosshead, the actuator assembly of the biomechanical device can impart both vertical and horizontal motion to the prosthetic connection assembly 52 to simulate a human motion, such as for example a human gait motion.

Referring to FIGS. 1 and 2, in exemplary embodiments, the prosthetic connection assembly is a lower leg assembly 52 that is configured to receive a lower limb prosthetic such as a prosthetic foot for testing with the biomechanical motion device 10. The lower leg assembly 52 includes an upper hinge 54 attached to the pivot shaft 50, and a lower rod 56 that extends from the upper hinge 54. With such configuration, the upper hinge 54 is rotatable about the pivot shaft 50, such that the lower rod 56 rotates or swings relative to the carriage 36. In this manner, the upper hinge 54 acts as a needle bearing mounted to the upper end of the lower rod that rotates about the simulated knee joint. The lower rod 56, therefore, operates as a simulated tibia. A standard prosthetic pyramid-style connector 58 is mounted to the other end of the of the lower rod 56 opposite from the upper hinge 54, to which a prosthetic foot 60 is attached for testing by the biomechanical motion device 10.

The biomechanical motion device further may include a heel stop block 62, which operates as a hard stop that restricts translational movement of the lower leg assembly 52 by virtue of movement of the carriage. The contact base 12 may be provided with a plurality or positioning holes 64, which may be pin holes or threaded fastening holes the may receive pins, screws, bolts or like fasteners that are attached to the stop block 62. The positioning holes may be configured with a linear or other suitable patterning to allow for adjustable positioning of the heel stop block 62 on the contact base 12. In general, the stop block 62 restricts translational movement of the lower leg assembly to impart rotation to the lower leg assembly in a first rotational direction when the carriage is moved toward the second carriage position. In this manner, the stop block 62 sets the position at which the heel of the prosthetic foot 60 contacts or strikes the contact base 12 during full retract and heel strike gait stages, as further detailed below. In the example as depicted in FIGS. 1 and 2, two sets of positioning holes are provided in the contact base to provide different positionings of the stop block 62 so as to accommodate different orientations of the lower leg assembly 52 with the prosthetic foot 60. Similarly, the horizontal cylinder mount 40 attached to the crosshead restricts translational movement of the lower leg assembly to impart rotation to the lower leg assembly in a second rotational direction opposite from the first rotational direction when the carriage is moved toward the first carriage position. This opposite rotation, as further detailed below, is imparted during full extend and toe off gait stages.

Figure 3:
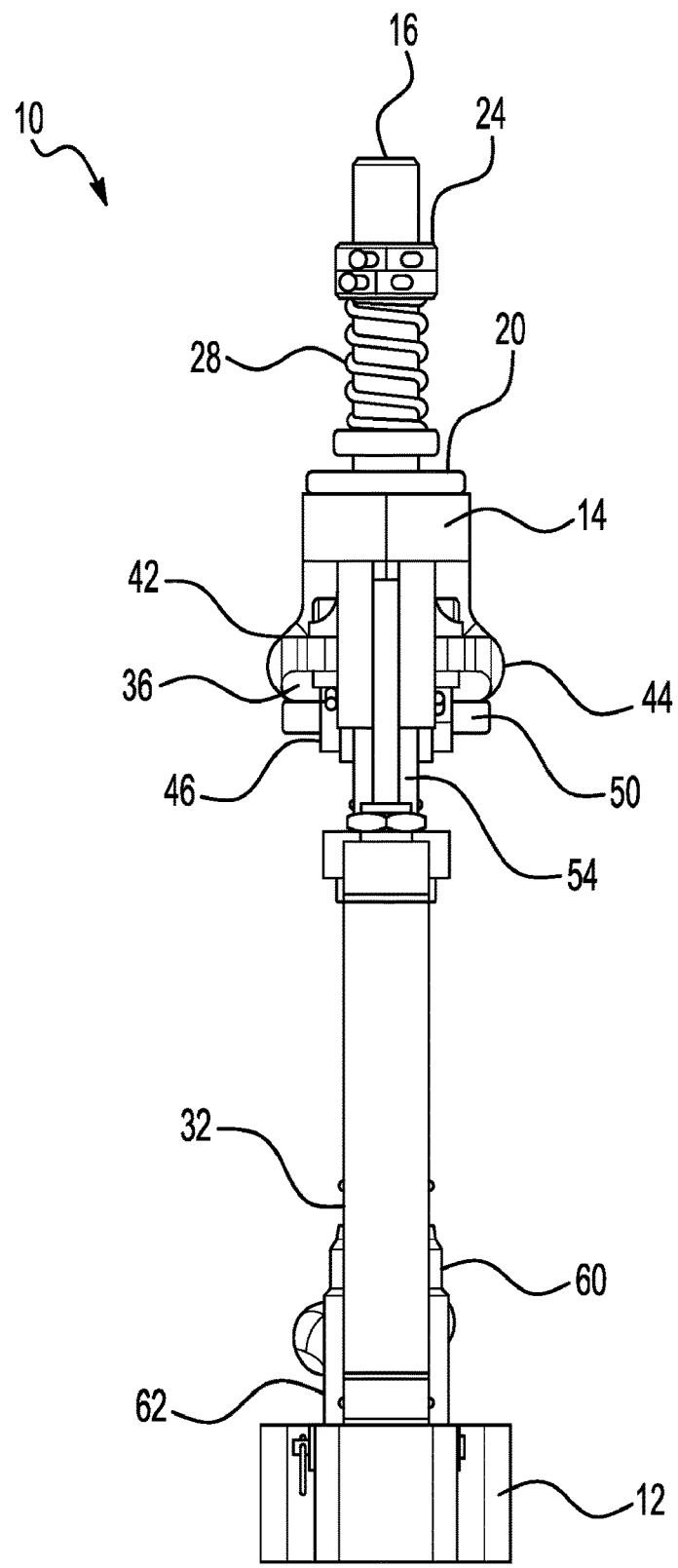
FIG. 3 is a drawing depicting an edge view of the biomechanical motion device of FIGS. 1 and 2.

FIG. 3 is a drawing depicting an edge view of the biomechanical motion device 10 of FIGS. 1 and 2 (particularly from the left side relative to the orientation of FIG. 1). FIG. 3 aids in illustrating the compactness of embodiments of the current application, as compared to conventional testing devices. Due to its compact size, including particularly the narrow width as illustrated in FIG. 3, multiple biomechanical motion devices 10 can be placed side by side within a relatively small area. In this manner, multiple devices can be positioned in parallel to each other within a same or common typical environment-controlled test chamber to test multiple prosthetic devices under different environmental conditions, such as for example different temperatures and humidity levels. In a non-limiting example, the biomechanical motion device 10 has dimensions of 30"×6"×29" (L×W×H), which permits the parallel positioning of multiple devices within a same or common environment-controlled test chamber.

Figure 4:
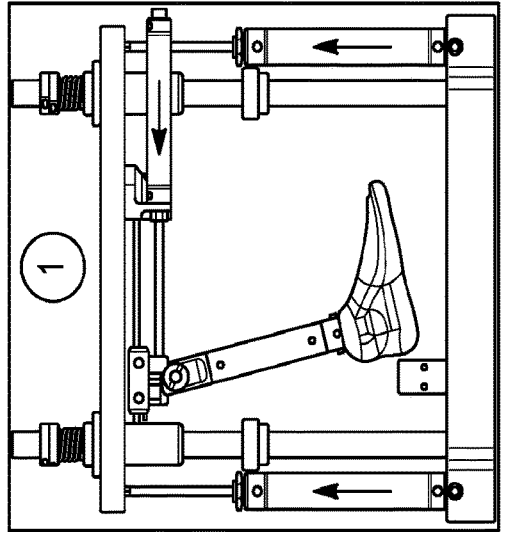
FIG. 4 is a drawing depicting stages one through six of simulated gait as implemented by the biomechanical motion device, in accordance with embodiments of the present application.
Figure 4:
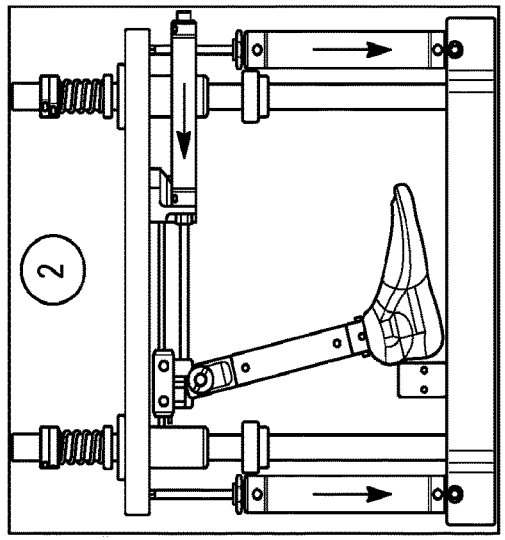
Figure 4:
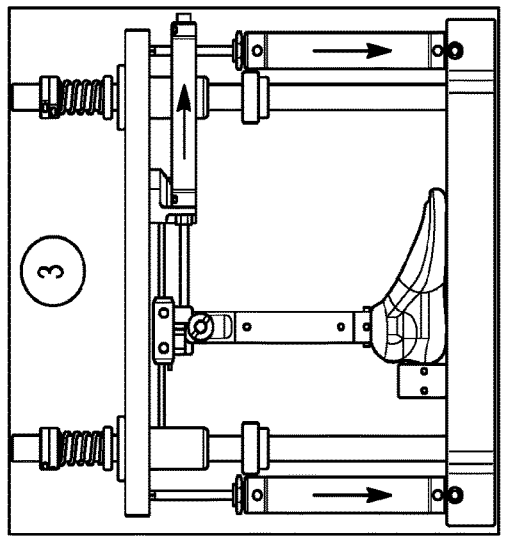
Figure 4:
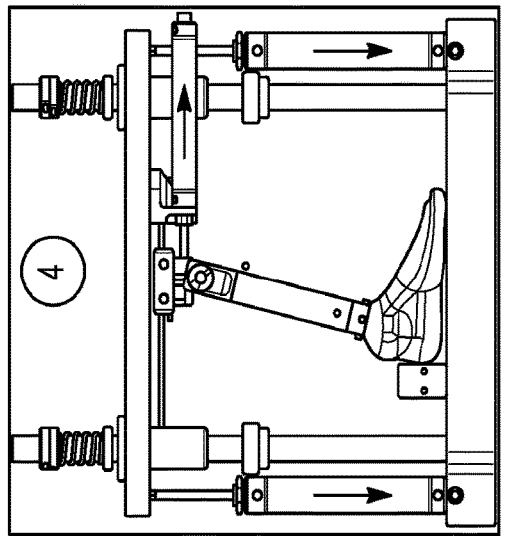
Figure 4:
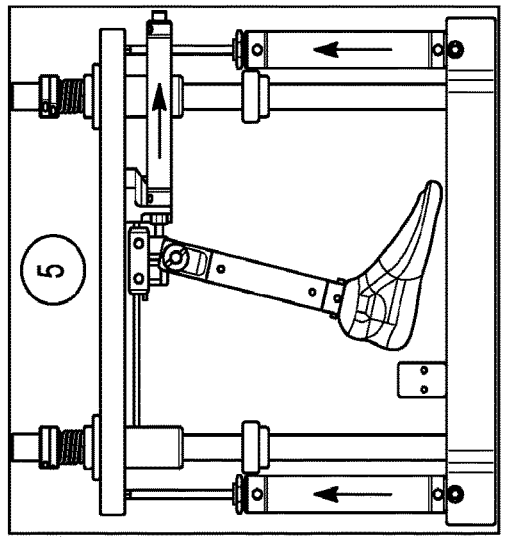
Figure 4:
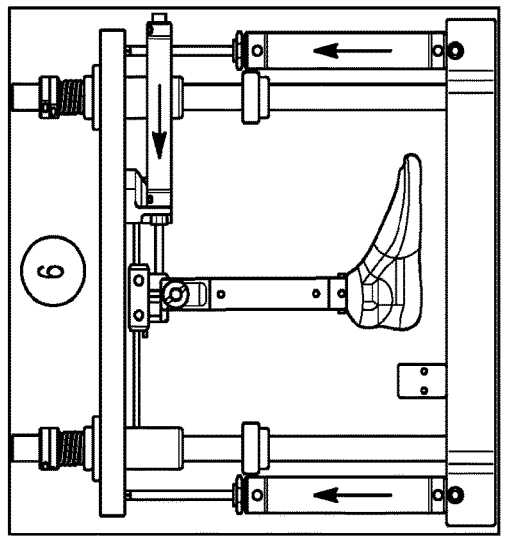
Figure 5:
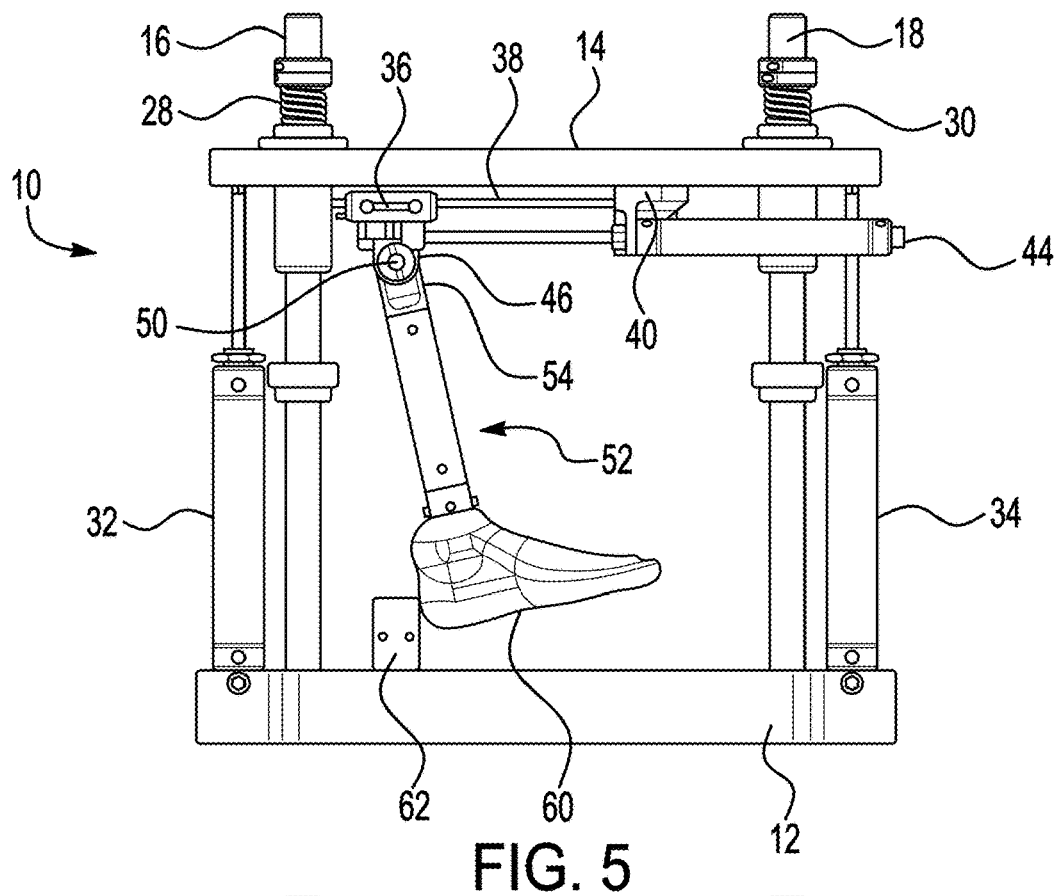
FIG. 5 is drawing depicting full retract, stage one, of FIG. 4 in isolation.

During operation to test a prosthetic device, the vertical cylinders 32 and 34 raise and lower the crosshead 14, applying vertical forces to the lower leg assembly 52 during the stance phase. The vertical cylinders 32 and 34 also lift the lower leg assembly 52 off from the bottom contact base 12 during the swing phase. Combined with such vertical movements, the horizontal cylinders 42 and 44 push and pull the lower leg assembly through the stages of gait to simulate the gait motion. The heel stop block 62 provides an additional block surface to aid in orienting the prosthetic foot 60 via the connection 58 relative to the rod 56, which further enhances the simulated gait motion. FIG. 4 is a drawing depicting exemplary stages one through six of a simulated gait cycle as implemented by the biomechanical motion device 10, in accordance with embodiments of the present application. FIGS. 5-10 are drawings depicting respectively each of the six stages illustrated in FIG. 4 in isolation, with the reference numerals limited to certain components for convenience of illustrating the various stages. It will be appreciated that each of the stages flow into one another, and thus the figures provide a generalized description of gait motion. Accordingly, intermediate stages between the six depicted stages will occur as the device transitions among the depicted stages. In addition, although FIG. 5 is denoted a first stage, the stages are cyclical and thus the designation of FIG. 5 as the initial stage is an arbitrary designation, as any stage may be considered the initial stage.

Stage 1 depicted in FIGS. 4 and 5 is referred to as full retract, insofar as the prosthetic foot 60 is in a retracted position relative to the base 12. In FIG. 4, the arrows indicate the pertinent states of the cylinders. In Stage 1, the vertical cylinders 32 and 34 are in an extended position relative to the base 12. With the vertical cylinders extended, the crosshead 14 is raised along the upright shafts 16 and 18 relative to the base 12 to the second crosshead position, thereby compressing the return springs 28 and 30. As a result, the prosthetic foot 60 is retracted, i.e. raised, from the base 12. Also in Stage 1, the horizontal cylinders 42 and 44 (as a side view only horizontal cylinder 44 is visible) are extended relative to the horizontal cylinder mount 40. As a result, the carriage 36 is moved leftward in the depicted orientation along the carriage rail 38 to the second carriage position. The extension of the horizontal cylinders drives the heel of the prosthetic foot 60 against the heel stop block 62, which blocks further translational motion of the prosthetic foot 60. As a result, the upper hinge 54 rotatably connected about the pivot shaft 50 rotates in a first rotational direction, and in this orientation the rotation is counterclockwise relative to a central position. The rotation of the upper hinge 54 imparts rotation to the additional components of the lower leg assembly 52 commensurately in the direction of rotation, thereby inclining the prosthetic foot 60 with the toe raised relative to the heel.

Figure 6:
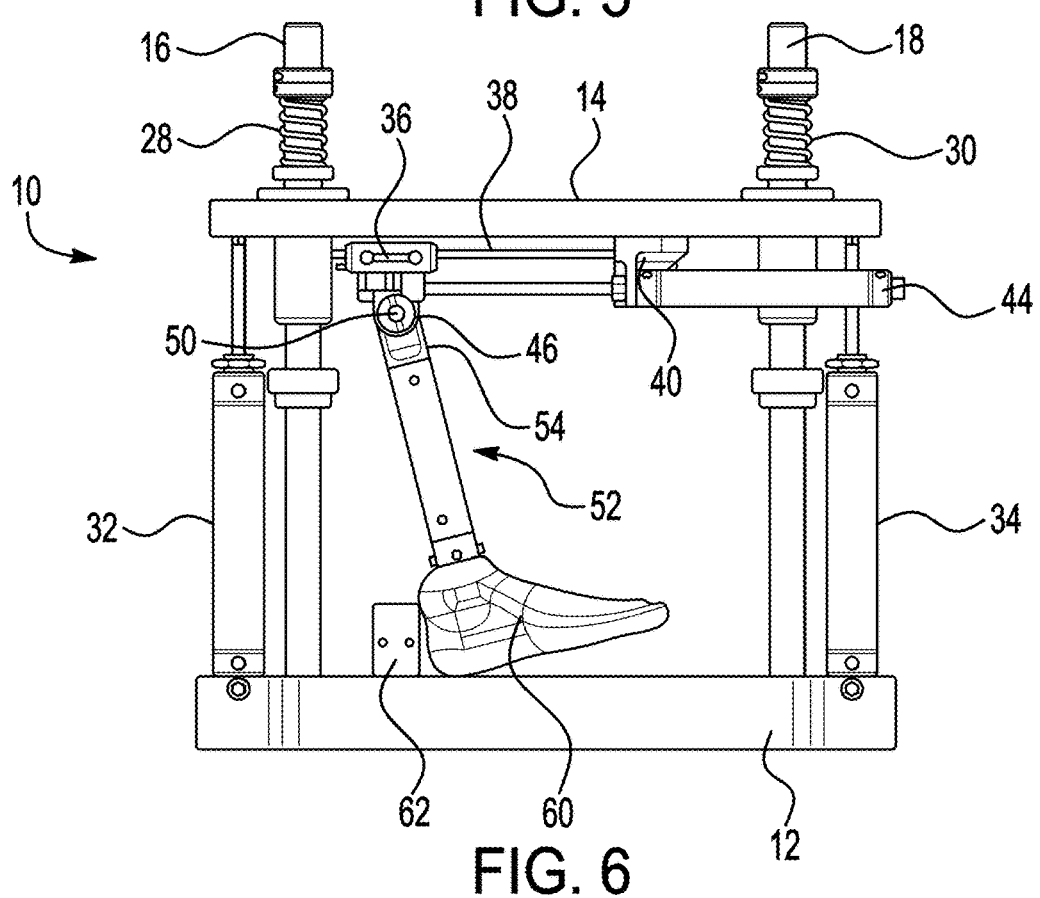
FIG. 6 is drawing depicting heel strike, stage two, of FIG. 4 in isolation.

Stage 2 depicted in FIGS. 4 and 6 is referred to as heel strike, insofar as the prosthetic foot 60 is positioned with the heel portion striking the base 12. In Stage 2, the vertical cylinders 32 and 34 are in a retracted position relative to the base 12. With the vertical cylinders retracted, the crosshead 14 is lowered along the upright shafts 16 and 18 relative to the base 12 (and lowered relative to the position of Stage 1) to the first crosshead position, thereby de-compressing the return springs 28 and 30. As a result, the prosthetic foot 60 is lowered toward the base 12. Also in Stage 2, similarly as in Stage 1, the horizontal cylinders 42 and 44 are extended relative to the horizontal cylinder mount 40. Again, as a result the carriage 36 is positioned leftward in the depicted orientation along the carriage rail 38 in the second carriage position. The extension of the horizontal cylinders still drives the heel of the prosthetic foot 60 against the heel stop block 62. As a result, the upper hinge 54 remains counterclockwise rotated maintaining the inclination of the prosthetic foot 60 with the toe raised relative to the heel. With the prosthetic foot lowered and inclined, the heel strikes the base 12 with the toe positioned out of contact with the base.

Figure 7:
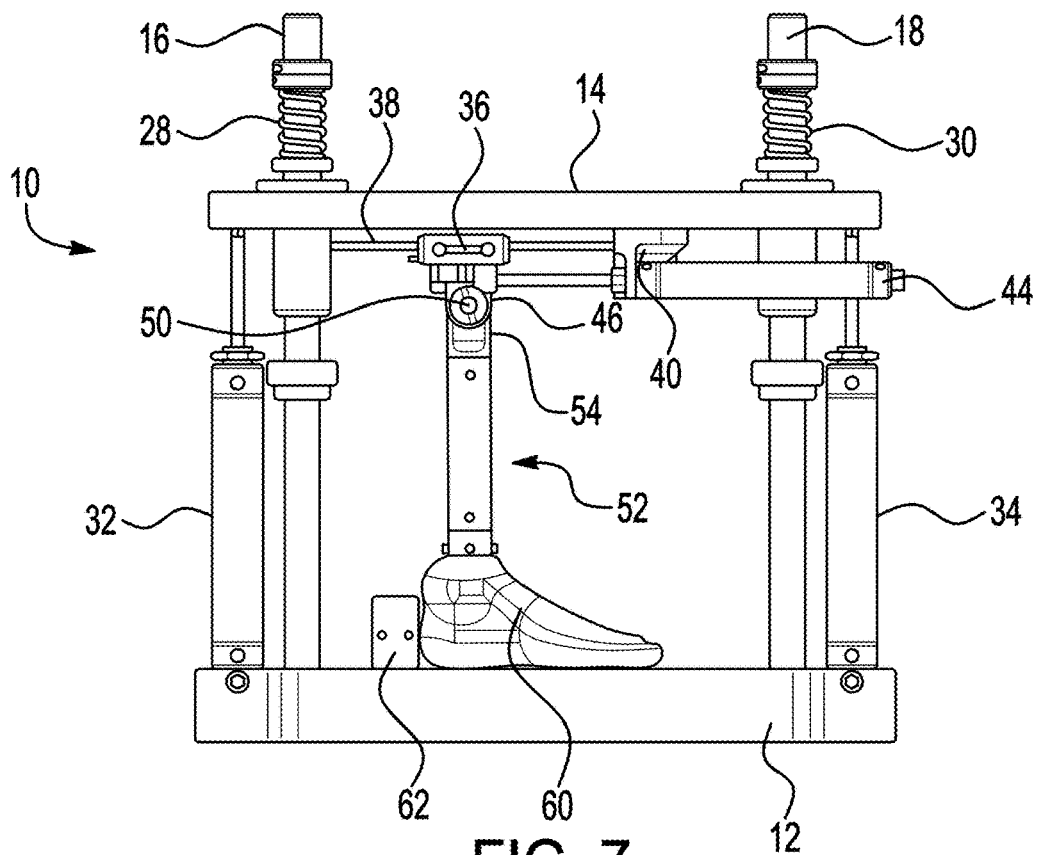
FIG. 7 is drawing depicting mid stance, stage three, of FIG. 4 in isolation.

Stage 3 depicted in FIGS. 4 and 7 is referred to as mid stance, insofar as the prosthetic foot 60 is positioned essentially flush with both heel and toe against the base 12. In Stage 3, similarly as in Stage 2, the vertical cylinders 32 and 34 remain in the retracted position relative to the base 12. With the vertical cylinders retracted, the crosshead 14 remains lowered in the first crosshead position along the upright shafts 16 and 18 relative to the base 12 (and lowered relative to the position of Stage 1), thereby de-compressing the return springs 28 and 30. As a result, the prosthetic foot 60 is lowered against the base 12. In Stage 3, the horizontal cylinders 42 and 44 are partially extended (or alternatively can be characterized as partially retracted) relative to the horizontal cylinder mount 40, being extended approximate midway between full extension and full retraction and thus essentially midway between the first carriage position and the second carriage position. As a result, the carriage 36 is moved rightward in the depicted orientation along the carriage rail 38 relative to the position of Stages 1 and 2. With only partial extension of the horizontal cylinders, the driving force of the heel of the prosthetic foot 60 against the heel stop block 62 is removed. As a result, the upper hinge 54 rotatably connected to the pivot shaft 50 rotates in a second or clockwise rotational direction relative to a center position, and the lower leg assembly 52 rotates commensurately such that the inclination of the prosthetic foot 60 is eliminated. Accordingly, the prosthetic foot lowers flush relative to the base 12 with the heel and toe now essentially positioned against the base 12.

When the biomechanical motion device 10 is transitioned smoothly through Stage 1 through Stage 3, a gait stepping motion is simulated. In ordinary human gait motion, when stepping the foot is lowered with the heel striking the ground first followed by a mid stance stage of the foot flush against the ground. Such stepping motion is therefore simulated by the biomechanical motion device 10 as the device transitions through Stages 1-3.

Figure 8:
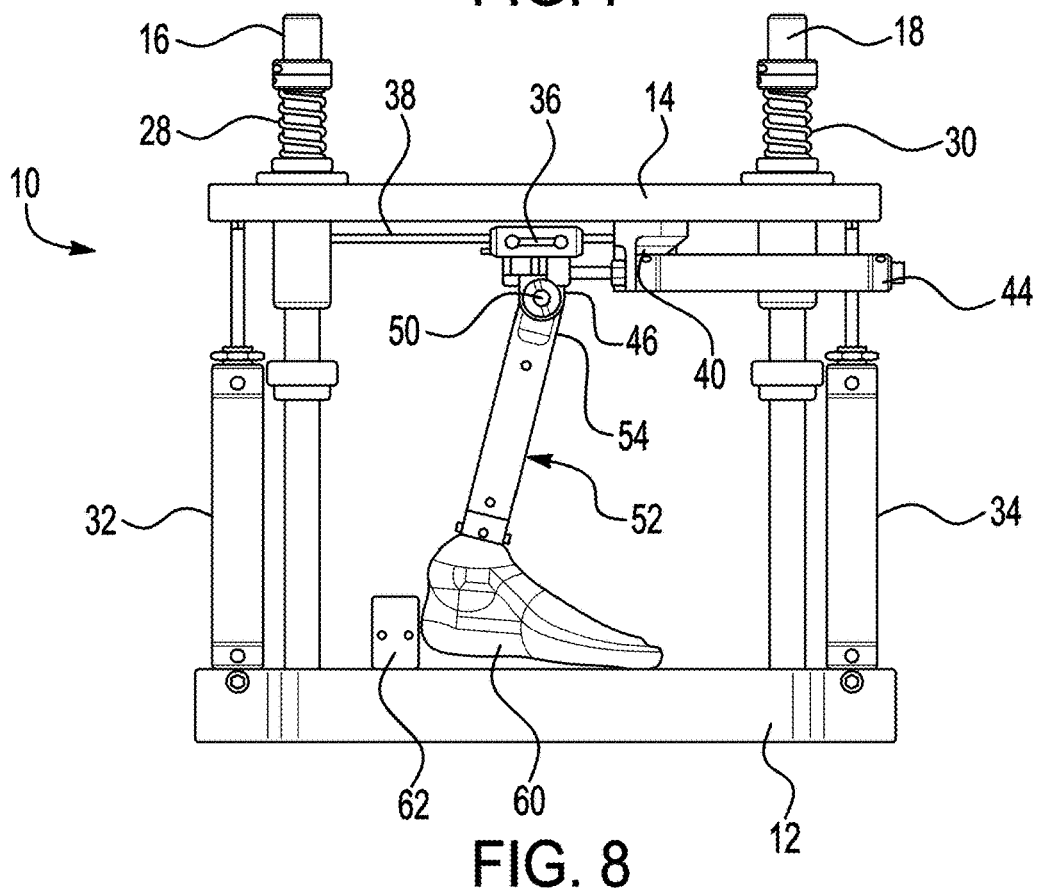
FIG. 8 is drawing depicting full extend, stage four, of FIG. 4 in isolation.

Stage 4 depicted in FIGS. 4 and 8 is referred to as full extend, insofar as the prosthetic foot 60 is in an extended position relative to the base 12. In Stage 4, the vertical cylinders 32 and 34 are in the retracted position relative to the base 12. With the vertical cylinders retracted, the crosshead 14 is lowered in the first crosshead position along the upright shafts 16 and 18 relative to the base 12, with the return springs 28 and 30 remaining decompressed. As a result, the prosthetic foot 60 remains in lowered in the position against the base 12. Also in Stage 4, the horizontal cylinders 42 and 44 are in the fully retracted position relative to the horizontal cylinder mount 40. As a result, the carriage 36 is moved further rightward in the depicted orientation along the carriage rail 38 relative to previous stages to the first carriage position. The retraction of the horizontal cylinders drives the bracket 46 against the horizontal mount 40. As a result, the upper hinge 54 rotates about the pivot shaft 50 in this orientation in the second clockwise direction relative to the central position, to swing the lower leg assembly 52 commensurately thereby inclining the prosthetic foot 60 with the heel raised relative to the toe.

Figure 9:
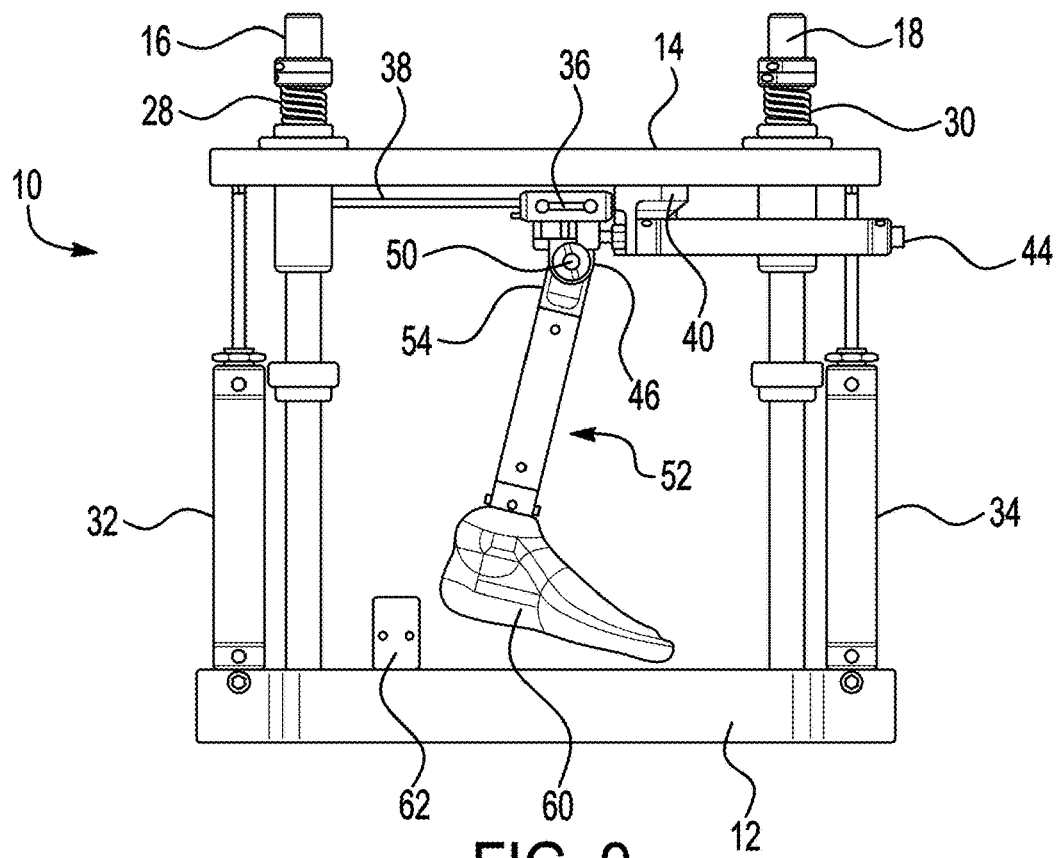
FIG. 9 is drawing depicting toe off, stage five, of FIG. 4 in isolation.

Stage 5 depicted in FIGS. 4 and 9 is referred to as toe off, insofar as the prosthetic foot 60 is positioned lifting off from the base 12. In Stage 5, the vertical cylinders 32 and 34 are in the extended position relative to the base 12. With the vertical cylinders extended, the crosshead 14 is raised along the upright shafts 16 and 18 relative to the base 12 to the second crosshead position, thereby compressing the return springs 28 and 30. As a result, the prosthetic foot 60 is raised from the base 12. Also in Stage 5, similarly as in Stage 4, the horizontal cylinders 42 and 44 are in the fully retracted position relative to the horizontal cylinder mount 40. As a result, the carriage 36 remains far rightward in the depicted orientation along the carriage rail 38 in the first carriage position. Again, the retraction of the horizontal cylinders drives the bracket 46 against the horizontal mount 40. As a result, the upper hinge 54 remains rotated in this orientation clockwise relative to the central position, thereby inclining the prosthetic foot 60 with the heel raised relative to the toe. Accordingly, the position of Stage 5 is referred to as toe off as the prosthetic foot remains inclined with the toe still pointing downward toward the base, and with the toe now moved off of the base subsequent to the heel raising off the base.

Figure 10:
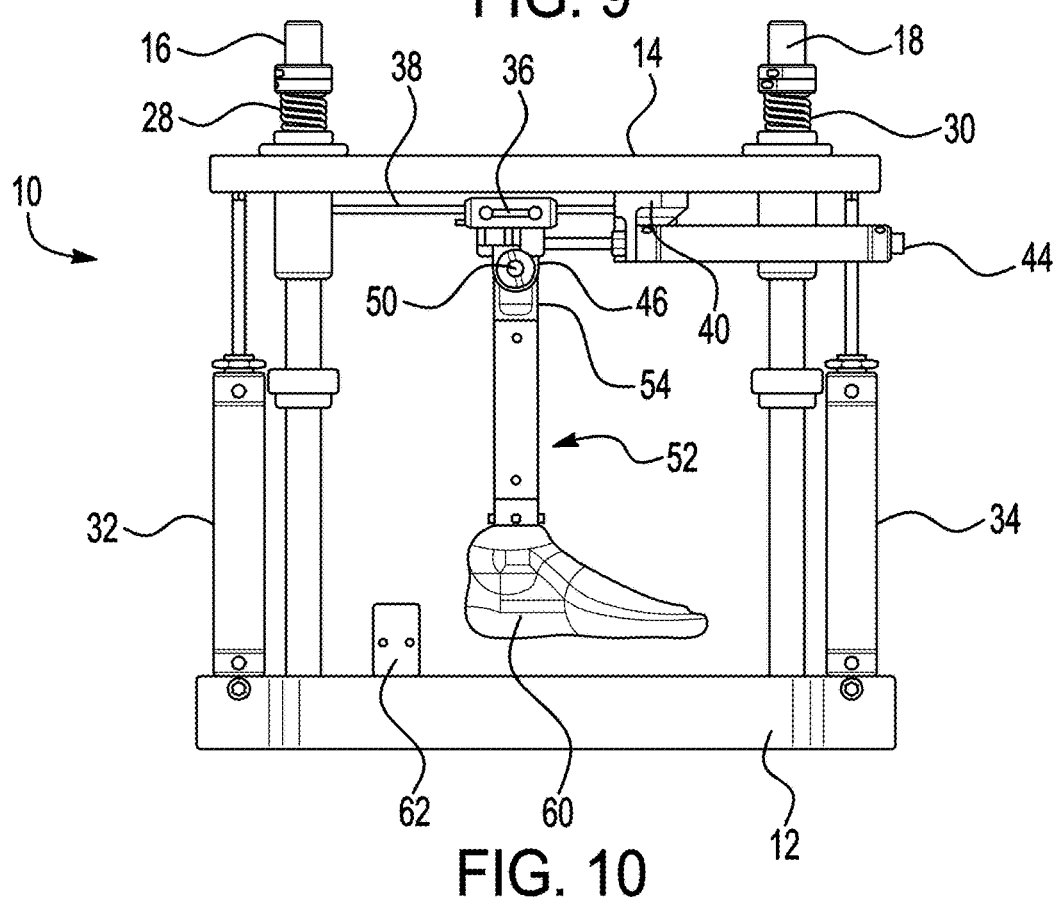
FIG. 10 is drawing depicting mid retract, stage six, of FIG. 4 in isolation.

Stage 6 depicted in FIGS. 4 and 10 is referred to as mid retract, insofar as the prosthetic foot 60 is positioned off of the base 12 (i.e., retracted from the base) with the prosthetic foot positioned essentially horizontally with the heel and toe aligned. In Stage 6, similarly as in Stage 5, the vertical cylinders 32 and 34 remain in the extended position relative to the base 12. With the vertical cylinders extended, the crosshead 14 remains raised in the second crosshead position along the upright shafts 16 and 18 relative to the base 12, thereby still compressing the return springs 28 and 30. As a result, the prosthetic foot 60 is raised from the base 12. In Stage 6, similarly as in Stage 3, the horizontal cylinders 42 and 44 are partially extended (or alternatively can be characterized as partially retracted) relative to the horizontal cylinder mount 40, being extended approximate midway between full extension and full retraction. As a result, the carriage 36 is moved leftward in the depicted orientation along the carriage rail 38 relative to the position of Stages 4 and 5 to a location essentially midway between the first carriage position and the second carriage position. With only partial extension of the horizontal cylinders, the driving force of the bracket 46 against the horizontal mount 40 is removed. As a result, the upper hinge 54 rotates counterclockwise about the pivot shaft 50 to the center position to swing the lower leg assembly 52, and the inclination of the prosthetic foot 60 is eliminated and the heel and toe become horizontally aligned.

When the biomechanical motion device 10 is transitioned smoothly from Stage 4 through Stage 6, a gait lift off motion is simulated. In ordinary human gait motion, when stepping from the ground the foot is raised with the heel coming off the ground first followed by the toe coming off the ground to a mid retracted stage of the foot horizontally positioned with the heel and toe horizontally aligned. Such stepping motion is therefore simulated by the biomechanical motion device 10 as the device transitions through Stages 4-6. Furthermore, after Stage 6 the biomechanical motion device 10 may be transitioned back to Stage 1 for repetition through Stages 1 through 6 in cyclical fashion. Repeated cycling simulates repeated stepping motion so as to simulate a walking gait through as many step cycles as desired for a particular testing protocol. As referenced above, the actuator cylinders may be controlled with a programmable logic controller (PLC) and four-way air directional control valves to implement a pre-programmed testing protocol of simulated gait, which can be used to test and evaluate the prosthetic foot or comparable device.

The various gate stages in relation to the biomechanical testing device operation can be summarized as follows. During the full retract stage, the at least one vertical cylinder is extended to position the crosshead in the second crosshead position, and the at least one horizontal cylinder is extended to position the carriage in the second carriage position. During the heel strike stage, the at least one vertical cylinder is retracted to position the crosshead in the first crosshead position, and the at least one horizontal cylinder is extended to position the carriage in the second carriage position. During the mid stance stage, the at least one vertical cylinder is retracted to position the crosshead in the first crosshead position, and the at least one horizontal cylinder is partially extended to position the carriage midway between the first carriage position and the second carriage position. During the full extend stage, the at least one vertical cylinder is retracted to position the crosshead in the first crosshead position, and the at least one horizontal cylinder is retracted to position the carriage in the first carriage position. During the toe off stage, the at least one vertical cylinder is extended to position the crosshead in the second crosshead position, and the at least one horizontal cylinder is retracted to position the carriage in the first carriage position. During the mid stance stage, the at least one vertical cylinder is extended to position the crosshead in the second crosshead position, and the at least one horizontal cylinder is partially extended to position the carriage midway between the first carriage position and the second carriage position. The lower leg assembly is rotated with the stop block in the first rotational direction to incline the prosthetic foot with the toe extending away from the contact base during full retract and heel strike. The lower leg assembly is rotated with the horizontal cylinder mount in the second rotational direction to incline the prosthetic foot with the toe extending toward the contact base during full extend and toe off. The gait cycle may be repeated through multiple and numerous cycles for evaluation and testing of a prosthetic device attached to the prosthetic connection assembly, such as for example a prosthetic foot attached to the lower leg assembly. Test protocols for various types of lower limb prosthetics, footwear, insoles, gait sensors, and the like may be implemented in this manner. As referenced above, it will be appreciated that each of the stages flow into one another, and thus the figures provide a generalized description of gait motion. Accordingly, intermediate stages between the six depicted stages will occur as the device transitions among the stages.

Accordingly, during operation to test a prosthetic device, the vertical cylinders raise and lower the crosshead, applying vertical forces to the lower leg assembly during the stance phase against the base. The vertical cylinders also lift the lower leg assembly off from the bottom contact base during the swing phase. The horizontal cylinders push and pull the lower leg through the stages of gait to simulate the gait motion. The vertical and horizontal sets of pneumatic cylinders are controlled using one or more four-way air directional control valves, and the timing and actuation of these valves is controlled using a PLC. As referenced above, the cadence is controlled through PLC programming, which controls the timing and duration of solenoid actuation of the control valves. Flow control is adjusted manually with a flow control screw present on the 4-way air directional control valves to adjust pneumatic flow, and in turn varying air pressure of each set of cylinders. Forces applied to the lower leg assembly thus are varied by changing pressure in each set of the vertical versus horizontal cylinders. The pressure in each set of cylinders is independently controlled with one pressure regulator for each set respectively of the vertical versus horizontal cylinders. In addition, due to the referenced compact size multiple biomechanical motion devices can be placed side by side within a relatively small area. In this manner, multiple devices can be positioned in parallel to each other within a same or common typical environment-controlled test chamber to test prosthetic devices under different environmental conditions, such as for example different temperatures and humidity levels.

Figure 11:
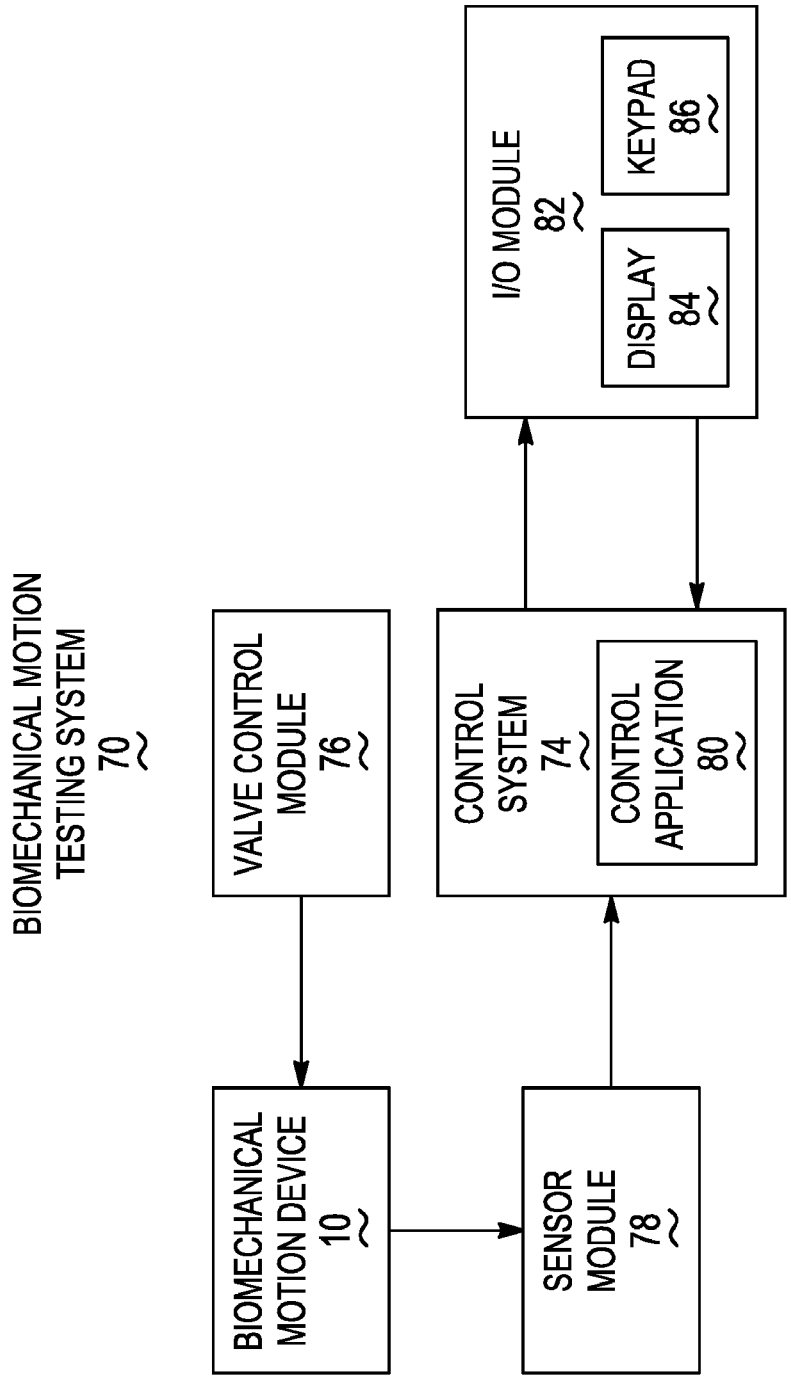
FIG. 11 is a schematic block diagram depicting operative portions of an exemplary biomechanical motion testing system in accordance with embodiments of the present application.

FIG. 11 is a schematic block diagram depicting operative portions of an exemplary biomechanical motion testing system 70 in accordance with embodiments of the present application. The testing system 70 includes a biomechanical motion device 10 as illustrated and described in connection with FIGS. 1-10, which is denoted in FIG. 11 as a block component for ease of illustration. The biomechanical motion device 10 is controllably coupled to a control system 74 that may be implemented using any suitable control interface. The control system 74 may control the biomechanical motion device 10 via operational control of a valve control module 76. As referenced above, the valve control module 76 may be configured as one or more four-way air directional control valves for controlling the vertical and horizontal sets of pneumatic cylinders. The control system 74 further may employ the referenced PLC control, whereby the cadence through the various gait stages is controlled through PLC programming. The testing system 70 further may include a sensor module 78 for sensing forces and positioning associated with the device being tested. Any suitable sensors may be employed as warranted for a particular testing protocol, including force sensors, pressure sensors, angle or position sensors, accelerometers, and the like. Sensor data is gathered from the prosthetic connection assembly and/or the prosthetic device (e.g., leg assembly to which a prosthetic foot is attached), and the sensor data may be used by the control system to assess performance of the prosthetic device based upon the sensor data.

The control system 74 may employ any suitable control electronics configured to carry out overall control of the functions and operations of the system, and well as the gathering and analysis of sensor information. The control system 74, therefore, may employ control electronics including an electronic processor such as a CPU, microcontroller or microprocessor. Among their functions, to implement the features of the present invention, the electronic processor may execute program code embodied as a testing control application 80 that may incorporate programming for any suitable testing protocols. It will be apparent to a person having ordinary skill in the art of computer programming, and specifically in application programming for analytical testing devices, how to program the code to operate and carry out logical functions associated with application 80. Accordingly, details as to specific programming code have been left out for the sake of brevity. The control application 80 may be stored in a non-transitory computer readable medium, such as random access memory (RAM), a read-only memory (ROM), an erasable programmable read-only memory (EPROM or Flash memory), or any other suitable medium that is incorporated as part of the control system 74. In the example of FIG. 11, the control application 80 is shown as being stored internally within the control system 74 as part of the processing components, but the application also may be stored in an additional or separate memory device. Also, while the code may be executed by control system 74 in accordance with an exemplary embodiment, such controller functionality could also be carried out via dedicated hardware, firmware, software, or combinations thereof, without departing from the scope of the invention.

The biomechanical motion testing system 70 also may include an input/output (I/O) module 82 that may include components to provide a suitable user interface. For example, the I/O module 82 may include a display 84 that displays information to a user regarding the various features and operating state of system, and displays visual content received or generated by the system. The I/O module 82 further may have a keypad 86 that provides for a variety of user input operations. For example, keypad 86 typically includes alphanumeric keys for allowing entry of alphanumeric information. Keys or key-like functionality also may be embodied as a touch screen associated with the display 84. Key functionality may be used for operating and executing the features of the control application 80 to devise, program, implement, and execute intended testing protocols.

An aspect of the invention, therefore, is a biomechanical motion device that has a compact configuration with effective simulation of a human motion, such as for example a human gait motion. In exemplary embodiments, the biomechanical motion device includes a contact base; at least one upright shaft that extends from the contact base; a crosshead spaced apart from the contact base and that is moveable relative to the contact base along the at least one upright shaft between a first crosshead position and a second crosshead position; a carriage rail attached to the crosshead so as to be moveable with the crosshead as the crosshead moves along the at least one upright shaft; a carriage that is slidably moveable along the carriage rail between a first carriage position and a second carriage position; a prosthetic connection assembly that is attached to the carriage so as to be moveable with the carriage as the carriage slides along the carriage rail, the prosthetic connection assembly being configured to receive a prosthetic device; and an actuator assembly configured to move the crosshead along the at least one upright shaft and the carriage along the carriage rail to move the prosthetic connection assembly through a plurality of stages that simulate a human motion. The biomechanical motion device may include one or more of the following features, either individually or in combination.

In an exemplary embodiment of the biomechanical motion device, a sliding direction of the carriage along the carriage rail is perpendicular to a movement direction of the crosshead along the at least one upright shaft.

In an exemplary embodiment of the biomechanical motion device, the actuator assembly comprises at least one vertical cylinder that drives movement of the crosshead along the at least one upright shaft, and at least one horizontal cylinder that drives movement of the carriage along the carriage rail.

In an exemplary embodiment of the biomechanical motion device, the at least one vertical cylinder includes a first vertical cylinder that extends between the contact base and the crosshead and is positioned adjacent to a first upright shaft, and a second vertical cylinder that extends between the contact base and the crosshead and is positioned adjacent to a second upright shaft.

In an exemplary embodiment of the biomechanical motion device, the at least one horizontal cylinder includes a first horizontal cylinder and a second horizontal cylinder that are mounted on opposite sides of a horizontal cylinder mount that is attached to the crosshead.

In an exemplary embodiment of the biomechanical motion device, each of the at least one vertical cylinder and the at least one horizontal cylinder is a pneumatic cylinder.

In an exemplary embodiment of the biomechanical motion device, the device further includes at least one return spring attached to the at least one upright shaft that biases the crosshead toward the first crosshead position.

In an exemplary embodiment of the biomechanical motion device, the prosthetic connection assembly is a lower leg assembly configured to receive a lower limb prosthetic, and the actuator assembly is configured to move the crosshead along the at least one upright shaft and the carriage along the carriage rail to move the lower leg assembly through a plurality of stages that simulate a human gait motion.

In an exemplary embodiment of the biomechanical motion device, the carriage further comprises a bracket that extends oppositely from the carriage rail and a pivot shaft that extends through the bracket, and the lower leg assembly includes a hinge rotatably connected to the pivot shaft and a lower rod that extends from the hinge, wherein the hinge is rotatable relative to the pivot shaft to rotate the lower leg assembly relative to the carriage.

In an exemplary embodiment of the biomechanical motion device, the device further includes a stop block connected to the contact base, wherein the stop block restricts translational movement of the lower leg assembly to impart rotation to the lower leg assembly in a first rotational direction when the carriage is moved toward the second carriage position.

In an exemplary embodiment of the biomechanical motion device, the contact base includes a plurality of positioning holes, and the stop block is repositionable in different positioning holes to adjust a connected position of the stop block to the contact base.

In an exemplary embodiment of the biomechanical motion device, the device further includes a mount attached to the crosshead, wherein the mount restricts translational movement of the lower leg assembly to impart rotation to the lower leg assembly in a second rotational direction opposite from the first rotational direction when the carriage is moved toward the first carriage position.

Another aspect of the invention is a biomechanical motion testing system that includes the biomechanical motion device accordingly to any of the embodiments, and an electronic control system configured to control the actuator assembly to move the prosthetic connection assembly through the plurality of stages that simulate the human motion. The biomechanical motion testing system may include one or more of the following features, either individually or in combination.

In an exemplary embodiment of the biomechanical motion testing system, the actuator assembly includes a plurality of pneumatic cylinders, and the biomechanical motion testing system further comprises a valve control module that is operated by the control system to control the actuator assembly.

In an exemplary embodiment of the biomechanical motion testing system, the control system includes a programmable logic controller (PLC) and the valve control module includes one or more four-way air directional control valves that control the plurality of pneumatic cylinders.

In an exemplary embodiment of the biomechanical motion testing system, the system further includes a sensor module that gathers sensor data from the prosthetic connection assembly and/or a connected prosthetic, and transmits the sensor data to the control system.

In an exemplary embodiment of the biomechanical motion testing system, the system further includes an input/output module comprising a user interface that receives user inputs that are transmitted to the control system and outputs information received from the control system.

Another aspect of the invention is a method of testing a prosthetic device that includes providing a biomechanical motion device according to any of the embodiments, and actuating the actuator assembly to move the prosthetic connection assembly through a plurality of stages that simulate a human motion. The method of testing may include one or more of the following features, either individually or in combination.

In an exemplary embodiment of the method of testing a prosthetic device, the method further includes gathering sensor data from the prosthetic connection assembly and/or the prosthetic device, and assessing a performance of the prosthetic device based upon the sensor data.

In an exemplary embodiment of the method of testing a prosthetic device, the prosthetic connection assembly is moved through the plurality of stages that simulate the human motion over multiple cycles.

In an exemplary embodiment of the method of testing a prosthetic device, the actuator assembly is configured to move the crosshead along the at least one upright shaft and the carriage along the carriage rail to move the lower leg assembly through a plurality of stages that simulate a human gait motion.

In an exemplary embodiment of the method of testing a prosthetic device, the actuator assembly comprises at least one vertical cylinder that drives movement of the crosshead along the at least one upright shaft and at least one horizontal cylinder that drives movement of the carriage along the carriage rail to simulate the human gait motion.

In an exemplary embodiment of the method of testing a prosthetic device, the lower limb prosthetic is a prosthetic foot, and the plurality of stages that simulate the human gait motion include full retract, heel strike, mid stance, full extend, toe off, and mid retract.

In an exemplary embodiment of the method of testing a prosthetic device, the method further includes rotating the lower leg assembly with the stop block in the first rotational direction to incline the prosthetic foot with the toe extending away from the contact base during full retract and heel strike.

In an exemplary embodiment of the method of testing a prosthetic device, the method further includes rotating the lower leg assembly with the mount in the second rotational direction to incline the prosthetic foot with the toe extending toward the contact base during full extend and toe off.

In an exemplary embodiment of the method of testing a prosthetic device, during the full retract stage, the at least one vertical cylinder is extended to position the crosshead in the second crosshead position, and the at least one horizontal cylinder is extended to position the carriage in the second carriage position.

In an exemplary embodiment of the method of testing a prosthetic device, during the heel strike stage, the at least one vertical cylinder is retracted to position the crosshead in the first crosshead position, and the at least one horizontal cylinder is extended to position the carriage in the second carriage position.

In an exemplary embodiment of the method of testing a prosthetic device, during the mid stance stage, the at least one vertical cylinder is retracted to position the crosshead in the first crosshead position, and the at least one horizontal cylinder is partially extended to position the carriage midway between the first carriage position and the second carriage position.

In an exemplary embodiment of the method of testing a prosthetic device, during the full extend stage, the at least one vertical cylinder is retracted to position the crosshead in the first crosshead position, and the at least one horizontal cylinder is retracted to position the carriage in the first carriage position.

In an exemplary embodiment of the method of testing a prosthetic device, during the toe off stage, the at least one vertical cylinder is extended to position the crosshead in the second crosshead position, and the at least one horizontal cylinder is retracted to position the carriage in the first carriage position.

In an exemplary embodiment of the method of testing a prosthetic device, during the mid stance stage, the at least one vertical cylinder is extended to position the crosshead in the second crosshead position, and the at least one horizontal cylinder is partially extended to position the carriage midway between the first carriage position and the second carriage position.

In an exemplary embodiment of the method of testing a prosthetic device, the method further includes varying pressure applied to each set of the at least on vertical cylinder and the at least one horizontal cylinder, wherein forces applied to the prosthetic connection assembly are varied by changing pressure in each set of the at least one vertical versus at least one horizontal cylinders.

In an exemplary embodiment of the method of testing a prosthetic device, pressure in each set of cylinders is independently controlled.

In an exemplary embodiment of the method of testing a prosthetic device, the method further includes placing at least one biomechanical motion device in an environmental chamber, and adjusting a temperature and/or a humidity to simulate different environmental conditions.

In an exemplary embodiment of the method of testing a prosthetic device, the method further includes placing a plurality of biomechanical motion devices in a same environmental chamber.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:
1. A biomechanical motion device comprising:
   a contact base;
   at least one upright shaft that extends from the contact base;
   a crosshead spaced apart from the contact base and that is moveable relative to the contact base along the at least one upright shaft between a first crosshead position and a second crosshead position;
   a carriage rail attached to the crosshead so as to be moveable with the crosshead as the crosshead moves along the at least one upright shaft;
   a carriage that is slidably moveable along the carriage rail between a first carriage position and a second carriage position;

a prosthetic connection assembly that is attached to the carriage so as to be moveable with the carriage as the carriage slides along the carriage rail, the prosthetic connection assembly being configured to receive a prosthetic device; and an actuator assembly configured to move the crosshead along the at least one upright shaft and the carriage along the carriage rail to move the prosthetic connection assembly through a plurality of stages that simulate a human motion.

2. The biomechanical motion device of claim 1, wherein a sliding direction of the carriage along the carriage rail is perpendicular to a movement direction of the crosshead along the at least one upright shaft.

3. The biomechanical motion device of claim 1, wherein the actuator assembly comprises at least one vertical cylinder that drives movement of the crosshead along the at least one upright shaft, and at least one horizontal cylinder that drives movement of the carriage along the carriage rail.

4. The biomechanical motion device of claim 3, wherein the at least one vertical cylinder includes a first vertical cylinder that extends between the contact base and the crosshead and is positioned adjacent to a first upright shaft, and a second vertical cylinder that extends between the contact base and the crosshead and is positioned adjacent to a second upright shaft.

5. The biomechanical motion device of claim 3, wherein the at least one horizontal cylinder includes a first horizontal cylinder and a second horizontal cylinder that are mounted on opposite sides of a horizontal cylinder mount that is attached to the crosshead.

6. The biomechanical motion device of claim 3, wherein each of the at least one vertical cylinder and the at least one horizontal cylinder is a pneumatic cylinder.

7. The biomechanical motion device of claim 1, further comprising at least one return spring attached to the at least one upright shaft that biases the crosshead toward the first crosshead position.

8. The biomechanical motion device of claim 1, wherein the prosthetic connection assembly is a lower leg assembly configured to receive a lower limb prosthetic, and the actuator assembly is configured to move the crosshead along the at least one upright shaft and the carriage along the carriage rail to move the lower leg assembly through a plurality of stages that simulate a human gait motion.

9. The biomechanical motion device of claim 8, wherein the carriage further comprises a bracket that extends oppositely from the carriage rail and a pivot shaft that extends through the bracket, and the lower leg assembly includes a hinge rotatably connected to the pivot shaft and a lower rod that extends from the hinge, wherein the hinge is rotatable relative to the pivot shaft to rotate the lower leg assembly relative to the carriage.

10. The biomechanical motion device of claim 9, further comprising a stop block connected to the contact base, wherein the stop block restricts translational movement of the lower leg assembly to impart rotation to the lower leg assembly in a first rotational direction when the carriage is moved toward the second carriage position.

11. The biomechanical motion device of claim 10, wherein the contact base includes a plurality of positioning holes, and the stop block is repositionable in different positioning holes to adjust a connected position of the stop block to the contact base.

12. The biomechanical motion device of claim 10, further comprising a mount attached to the crosshead, wherein the mount restricts translational movement of the lower leg assembly to impart rotation to the lower leg assembly in a second rotational direction opposite from the first rotational direction when the carriage is moved toward the first carriage position.

13. A biomechanical motion testing system comprising:
the biomechanical motion device of claim 1; and
an electronic control system configured to control the actuator assembly to move the prosthetic connection assembly through the plurality of stages that simulate the human motion.

14. The biomechanical motion testing system of claim 13, wherein the actuator assembly includes a plurality of pneumatic cylinders, and the biomechanical motion testing system further comprises a valve control module that is operated by the control system to control the actuator assembly.

15. The biomechanical motion testing system of claim 14, wherein the control system includes a programmable logic controller (PLC) and the valve control module includes one or more four-way air directional control valves that control the plurality of pneumatic cylinders.

16. The biomechanical motion testing system of claim 13, further comprising a sensor module that gathers sensor data from the prosthetic connection assembly and/or a connected prosthetic, and transmits the sensor data to the control system.

17. The biomechanical motion testing system of claim 13, further comprising an input/output module comprising a user interface that receives user inputs that are transmitted to the control system and outputs information received from the control system.

18. A method of testing a prosthetic device comprising the steps of;
providing a biomechanical motion device comprising:
a contact base;
at least one upright shaft that extends from the contact base;
a crosshead spaced apart from the contact base and that is moveable relative to the contact base along at the least one upright shaft between a first crosshead position and a second crosshead position;
a carriage rail attached to the crosshead so as to be moveable with the crosshead as the crosshead moves along the at least one upright shaft;
a carriage that is slidably moveable along the carriage rail between a first carriage position and a second carriage position;
a prosthetic connection assembly that is attached to the carriage so as to be moveable with the carriage as the carriage slides along the carriage rail, the prosthetic connection assembly being configured to receive a prosthetic device; and
an actuator assembly configured to move the crosshead along the at least one upright shaft and the carriage along the carriage rail to move the prosthetic connection assembly;
attaching the prosthetic device to the prosthetic connection assembly; and
actuating the actuator assembly to move the prosthetic connection assembly through a plurality of stages that simulate a human motion.

19. The method of testing a prosthetic device of claim 18, wherein the prosthetic connection assembly is a lower leg assembly configured to receive a lower limb prosthetic, and the actuator assembly is configured to move the crosshead along the at least one upright shaft and the carriage along the carriage rail to move the lower leg assembly through a plurality of stages that simulate a human gait motion.

20. The method of testing a prosthetic device of claim 18, further comprising placing at least one biomechanical motion device in an environmental chamber, and adjusting a temperature and/or a humidity to simulate different environmental conditions.

* * * * *